United States Patent [19]

Brown et al.

[11] Patent Number: 5,488,186

[45] Date of Patent: Jan. 30, 1996

[54] GAS PHASE PROCESS FOR THE HYDRATION OF PROPYLENE

[75] Inventors: Stephen H. Brown, Princeton, N.J.; Jeffrey C. Trewella, Kennett Square, Pa.

[73] Assignee: Mobil Oil Corporation, Fairfax, Va.

[21] Appl. No.: 408,244

[22] Filed: Mar. 22, 1995

[51] Int. Cl.$^6$ ............................ C07C 29/04; C07C 31/10
[52] U.S. Cl. ........................................ 568/897; 568/695
[58] Field of Search ................................................ 568/897

[56] References Cited

U.S. PATENT DOCUMENTS

| | | | |
|---|---|---|---|
| 2,830,090 | 4/1958 | Teter et al. | 568/897 |
| 4,214,107 | 7/1980 | Chang et al. | 568/897 |
| 4,783,555 | 11/1988 | Atkins | 568/897 |
| 4,886,918 | 12/1989 | Sorensen et al. | 568/897 |
| 4,967,020 | 10/1990 | Marler et al. | 568/897 |
| 5,144,086 | 9/1992 | Harandi et al. . | |

*Primary Examiner*—Joseph E. Evans
*Attorney, Agent, or Firm*—A. J. McKillop; M. D. Keen

[57] ABSTRACT

A process is presented for the hydration of light olefins to produce $C_2$–$C_7$ aliphatic alcohols with improved selectivity, catalyst productivity and catalyst stability. Acidic medium pore, shape selective metallosilicate catalyst particles are contacted with a feedstream containing light olefin plus water at elevated temperature above the dew point of water, i.e., in a gas phase, wherein the reaction mixture is essentially starved with respect to the mole ratio of water to $C_2$–$C_7$ light olefin. Isopropanol is produced at a selectivity greater than 70 weight percent when the mole ration of water to propylene is between 0.05 and 0.499. Zeolite ZSM-5, ZSM-23, ZSM-35 and ferrierite are preferred catalysts.

10 Claims, 1 Drawing Sheet

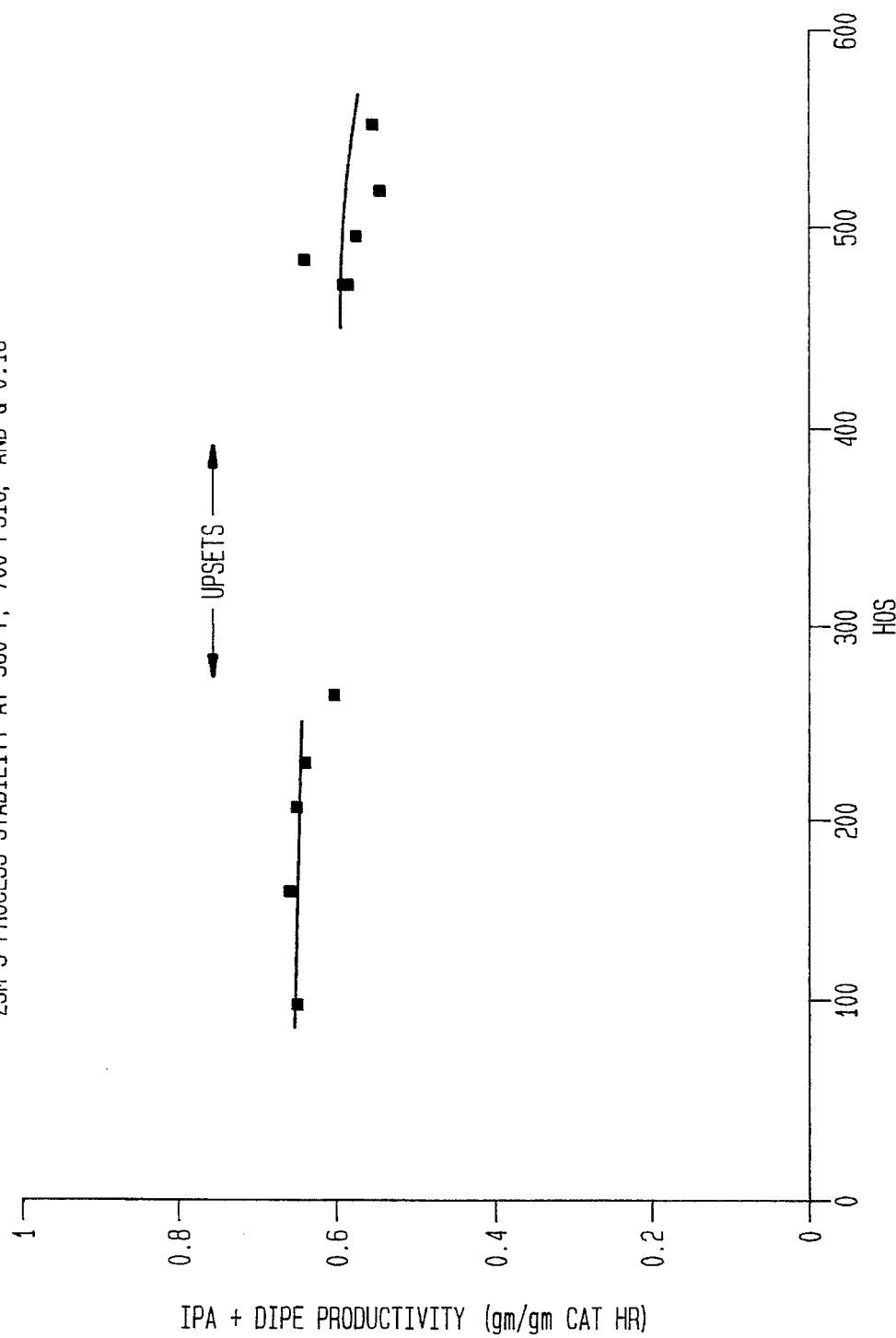

GAS PHASE PROCESS FOR THE HYDRATION OF PROPYLENE

FIELD OF THE INVENTION

This invention relates to a process for the production of isopropanol (IPA) from propylene and water. The invention particularly relates to a process for the production of isopropanol by hydration of propylene in a gas phase employing medium pore size, shape selective zeolite catalyst. The invention especially relates to a method for propylene hydration with water in contact with zeolite catalysts such as ZSM-5, ZSM-23, ZSM-35 and Ferrierite under conditions which provide high selectivity for IPA and high catalyst productivity.

BACKGROUND OF THE INVENTION

There is a need for an efficient catalytic process to manufacture ethers from linear monoolefins, thereby augmenting the supply of high-octane blending stock for gasoline. The C5+ lower molecular weight ethers, such as methyl sec-amyl ether, are in the gasoline boiling range. Lower molecular weight alcohols and ethers such as isopropyl alcohol (IPA) and diisopropyl ether (DIPE) are also in the gasoline boiling range and are known to have a high blending octane number. In addition, by-product propylene and butylenes are usually available in a fuels refinery. The petrochemicals industry also produces linear olefin streams in the C2 to C15 molecular weight range, and the conversion of such streams or fractions thereof to ethers can provide products useful as solvents and as blending stocks for fuel.

The catalytic hydration of olefins, particularly $C_3$ olefin, to provide alcohols and ethers is a well-established art. Representative olefin hydration processes are disclosed in U.S. Pat. Nos. 2,262,913, 2,477,380, 2,797,247, 3,798,097, 2,805,260, 2,830,090, 2,861,045, 2,891,999, 3,006,970, 3,198,752, 3,810,848, 3,989,762, among others.

Olefin hydration employing medium pore and large pore zeolite catalyst is a known synthesis method. As disclosed in U.S. Pat. No. 4,214,107 (Chang et al.), incorporated herein by reference, lower olefins, in particular propylene, are catalytically hydrated over a crystalline aluminosilicate zeolite catalyst having a silica to alumina ratio of at least 12 and a Constraint Index of from 1 to 12, e.g., acidic ZSM-5 type zeolite, to provide the corresponding alcohol, essentially free of ether and hydrocarbon by-product. Acid resin catalysts such as "Amberlyst 15" may also be used for hydration of light olefins.

Recently, processes for the hydration of olefins to provide alcohols and ethers using zeolite catalyst such as ZSM-5 or zeolite Beta have been disclosed in U.S. Pat. Nos. 4,499,313 to Bell et al.; and U.S. Pat. Nos. 4,757,664, 4,857,664 and 4,906,187 to T. Huang. One of the advantages in using zeolite catalyst for hydration and/or etherification of light olefins is the regenerability of the catalyst. Where resin based catalysts can decompose at the high temperatures required to remove deactivating amounts of carbonaceous deposits, zeolite catalysts remain thermally stable and can be regenerated oxidatively or in contact with hydrogen.

According to U.S. Pat. No. 4,499,313, an olefin is hydrated to the corresponding alcohol in the presence of hydrogen-type mordenite or hydrogen-type zeolite Y each having a silica-alumina molar ratio of 20 to 500. The use of such a catalyst is said to result in higher yields of alcohol than olefin hydration processes which employ conventional solid acid catalysts. Use of the catalyst is said to offer the advantage over ion-exchange type olefin hydration catalysts of not being restricted by the hydration temperature.

European Patent Application 210,793 describes an olefin hydration process employing a medium pore zeolite as hydration catalyst. Specific catalysts mentioned are Theta-1, said to be preferred, ferrierite, ZSM-22, ZSM-23 and NU-10.

Formation of the initial carbon-oxygen bond in an alcohol by olefin hydration, such as the formation of isopropanol by hydration of propene, is a difficult step that puts severe demands on acid catalyst stability. These stability problems are due to hydrolysis of the active catalyst sites by liquid-phase water, and appear common to acidic resin, sulfuric acid, and zeolite catalysts.

It is known that medium pore, shape selective zeolite catalysts show a relatively low activity and reduced stability in propylene hydration processes. The role of water in contributing to the diminished activity of zeolite catalysts in propylene hydration is recognized. However, since water is a necessary reactant in the process, new methods to overcome the deleterious effects of water on catalyst while producing high IPA selectivity and catalyst activity have eluded discovery.

It is an objective of the present invention to provide a process for the production of isopropanol from propylene with high selectivity and catalyst life.

It is a further object of the present invention to provide a process for the production of IPA using medium pore, shape selective metallosilicate catalyst under conditions wherein catalyst activity is enhanced and catalyst productivity improved.

Yet a further objective of the present invention is to provide a process for the production of IPA using acidic zeolite catalysts such as ZSM-5, ZSM-23, ZSM-35 and Ferrierite under conditions of high catalyst activity, selectivity and stability.

SUMMARY OF THE INVENTION

A process has been discovered for the hydration of light olefins to produce $C_3$–$C_6$ aliphatic alcohols with improved selectivity, catalyst productivity and catalyst stability. The process uses medium pore, shape selective metallosilicate catalyst particles in contact with a feedstream containing light olefin plus water. When these components of the process are caused to react at elevated temperature above the dew point of water, i.e., in a gas phase, wherein the reaction mixture is essentially starved with respect to the mole ratio of water to $C_3$–$C_6$ light olefin the propensity for catalyst to become deactivated is overcome and a process for producing a high selectivity of alcohol production is established. Equally important, it has been discovered that under olefin hydration reaction conditions essentially starved with respect to water in contact with the zeolite catalyst, catalyst productivity is greatly improved and catalyst active life is extended.

The invention specifically comprises a process for the production of isopropanol with high selectivity, high catalyst productivity and long catalyst life by contacting water and a feedstream comprising propylene in the gas phase with acidic medium pore, shape selective metallosilicate catalyst particles under propylene hydration conditions at a water:propylene mole ratio between 0.05 and 0.499. Isopropanol is produced at a selectivity of at least 70 weight percent and catalyst productivity is at least 0.1 unit weight of oxygenates, particularly IPA and diisopropyl ether (DIPE), per unit weight of catalyst per hour.

The preferred catalyst comprises acidic ZSM-5 and a mole ratio of water to propylene between 0.18 and 0.33.

DETAILED DESCRIPTION OF THE INVENTION

The Figure is a graph plotting IPA+DIPE productivity versus hours-on-stream for the process of the invention.

DETAILED DESCRIPTION OF THE INVENTION

Prior work in the hydration of propylene with water to produce IPA in contact with medium pore, shape selective zeolite catalyst particles has shown that under a wide range of experimental conditions acidic ZSM-5 has low activity and poor stability for propylene hydration to IPA. A theoretical analysis of the problem has led to the conclusion, seminal to the discovery of the instant invention, that excess water is responsible for the poor performance. The poor activity is accounted for by the selective sorption of water from propylene/water feedstocks and the poor stability is due to the presence of an aqueous phase which dissolves the zeolite and, thereby, lowers the number of effective catalyst sites. Nevertheless, it has been generally held in the prior art that excess water is a necessary component of the operating conditions for propylene hydration to promote: IPA formation; high per pass propylene conversion under equilibrium conditions; and to prevent catalyst coking. Equilibrium considerations favor low temperature, high pressure, and high water:propylene mole ratio. At a low water to propylene ratio DIPE production was generally believed to be inevitable because DIPE dominates the equilibrium composition. Therefore, it had appeared that the solution to the problem of zeolite catalyst activity in propylene hydration could only be purchased at the expense of IPA selectivity and low per pass conversion rates. Additionally, it had appeared that the solution to the problem of zeolite catalyst stability was not achievable. At high water to olefin ratio the zeolite dissolved and at low water to olefin ratio it would coke.

The essence of the invention disclosed herein is the finding that by using medium pore zeolites with low water-:propylene mole ratio feedstocks the foregoing limitations of medium pore size, shape selective zeolite catalysts in light olefin hydration processes, especially propylene and butylene hydration, are overcome and the following improvements are achieved:

* Activity can be increased 10 to 100-fold even though the reaction is "starved" for one reactant (water).

* Catalyst stability can be improved 10 to 100-fold even though the large excess of propylene was expected to promote propylene oligomerization, leading to carboneaous coke.

* High IPA selectivity can be maintained even though equilibrium favors DIPE formation.

Results derived from the present invention show that the activity and stability of medium pore zeolites improve dramatically when the propylene hydration process is carried out in the gas phase at water:propylene mole ratios below 0.4. Excellent IPA selectivity can be obtained due to the shape selectivity of medium pore zeolites which depress the rate of DIPE formation.

Contrary to expectations based on prior results, the present invention shows that medium pore zeolites are excellent candidates for propylene hydration. IPA can be selectively produced at >1.0 gm IPA/gm catalyst hr, which is nearly ten times the productivity of current commercial processes. In addition to increased productivity, zeolites are non-corrosive, thermally stable, regenerable, and environmentally friendly.

The present invention is applicable to the conversion of individual light olefins and mixtures of olefins of various structures, preferably light olefins within the $C_2$–$C_7$ range, to alcohols. Accordingly, the invention is applicable to the conversion of ethylene, propylene, butenes, pentenes, hexenes, and heptenes, mixtures of these and other olefins such as gas plant off-gas containing ethylene and propylene, naphtha cracker off-gas containing light olefins, fluidized catalytic cracker (FCC) light gasoline containing pentenes, hexenes and heptenes, refinery FCC propane/propylene streams, etc. However, the invention is particularly applicable to the hydration of propylene to IPA and butenes to 2-butanol.

In the process to prepare IPA, a feedstock comprising propene or a refinery $C_3$ hydrocarbon stream comprising olefins and paraffins, i.e., propene and propane, is contacted at elevated pressure with an acidic zeolite catalyst and water as a reactant to hydrate propene to form isopropanol (IPA) with diisopropyl ether (DIPE) produced as a minor by-product. Minor amounts of oligomerization products of propene are also formed in the acidic catalyst environment, particularly hexenes and nonenes. On a per pass basis, the conversion of propene generally is about 5%, or between 4% and 10% with IPA selectivity of at least 70 weight percent. The effluent from the hydration zone is conventionally passed to a fractionator wherein a bottom stream is separated containing IPA and DIPE by-product and an overhead stream that contains the unreacted $C_3$ hydrocarbons comprising propene and propane, if an olefin and paraffin feedstock has been used. The $C_3$ stream, typically containing both propene and propane, can be recompressed and recycled to the IPA reactor.

The operating conditions of the olefin hydration and etherification process include a temperature between 50° C. and 450° C., pressure between 700 kPa and 24,000 kPa and weight hourly space velocity based on catalyst between 0.1 and 10. The preferred conditions are a temperature between 150° C. and 250° C., pressure between 2800 kPa and 7000 Kpa and weight hourly space velocity between 1 and 10.

An especially critical element of the operating conditions in the process of the instant invention is the mole ratio of water to propylene. It is important that the process of the invention operate in the gas phase and, to meet that parameter, it is required that the process operate below the dew point of water. Therefore, the combined operating conditions of temperature and pressure and the selected ratio of water and propylene are determined to meet the foregoing requirement. The mole ratio of water:propylene in the instant process can be between 0.05 and 0.499. However, the preferred mole ration is between 0.1 and 0.35 and, most preferably, between 0.18 and 0.33.

The catalyst employed in the olefin hydration operations of the present invention is medium pore, shape-selective acidic zeolite catalyst. The hydration zone catalyst is selected from the group consisting of ZSM-5, ZSM-11, ZSM-22, ZSM-23, ZSM-35, ZSM-48, MCM-22 and Ferrierite. The preferred catalysts are ZSM-5, ZSM-23, ZSM-35 and Ferrierite. The most preferred catalyst is acidic ZSM-5.

ZSM-5 is disclosed and claimed in U.S. Pat. No. 3,702,886 and U.S. Pat. No. Re. 29,948;

ZSM-11 is disclosed and claimed in U.S. Pat. No. 3,709,979.

ZSM-22 is more particularly described in U.S. Pat. No. 4,046,859, the entire contents of which are incorporated herein by reference.

ZSM-23 is more particularly described in U.S. Pat. No. 4,076,842, the entire contents of which are incorporated herein by reference.

ZSM-35 is more particularly described in U.S. Pat. No. 4,016,245, the entire contents of which are incorporated herein by reference.

MCM-22 is described in U.S. Pat. No. 4,954,325 to M. K. Rubin and P. Chu, issued Sep. 4, 1990.

The hydration of propene is particularly described in the previously referenced U.S. Pat. No. 4,967,020. This patent teaches that high selectivity can be achieved in the production of IPA or other alcohols using acidic zeolite catalyst of relatively small crystal size of not more than 0.2 micron. The catalyst employed is a relatively constrained intermediate pore size zeolite exhibiting a Constraint Index in the range of 1–12, as determined by the method described in U.S. Pat. No. 4,016,218. The zeolites which are actually used in the present process are also characterized by specific sorption properties related to their relatively constrained diffusion characteristics. These sorption characteristics are those which are set out in U.S. Pat. No. 4,810,357, incorporated herein by reference, for the zeolites such as ZSM-22, ZSM-23, ZSM-35 and ferrierite.

The zeolite hydration catalyst selected for use herein will generally possess an alpha value of at least about 1, preferably at least 10 and more preferably at least about 50. "Alpha value", or "alpha number", is a measure of zeolite acidic functionality and is more fully described together with details of its measurement in U.S. Pat. No. 4,016,218, J. Catalysis, 6, pp. 278–287 (1966) and J. Catalysis, 61, pp. 390–396 (1980). Variation of zeolites acidity can be achieved by a variety of techniques including (a) synthesizing a zeolite with different silica/alumina ratios, (b) steaming, (c) steaming followed by dealuminization and (d) substituting framework aluminum with other species. For example, in the case of steaming, the zeolite(s) can be exposed to steam at elevated temperatures ranging from about 500° F. to about 1200° F. and preferably from about 750° to about 1000° F. This treatment can be accomplished in an atmosphere of 100% steam or an atmosphere consisting of steam and a gas which is substantially inert to the zeolite. A similar treatment can be accomplished at lower temperatures employing elevated pressure, e.g., at from about 350° to about 700° F. with about 1030 kPa to about 20,600 kPa. Specific details of several steaming may be gained from the disclosures of U.S. Pat. Nos. 4,325,994; 4,374,296; and 4,418,235, the contents of which are incorporated by reference herein. Aside from, or in addition to any of the foregoing procedures, the surface acidity of the zeolite(s) can be eliminated or reduced by treatment with bulky reagents as described in U.S. Pat. No. 4,520,221, the contents of which are incorporated by reference herein.

In practicing the olefin hydration process of the present invention, it can be advantageous to incorporate the zeolite into some other material, i.e., a matrix or binder, which is resistant to the temperature and other conditions employed in the process. Useful matrix materials include both synthetic and naturally-occurring substances, e.g., inorganic materials such as clay, silica and/or metal oxides. Such materials can be either naturally-occurring or can be obtained as gelatinous precipitates or gels including mixtures of silica and metal oxides. Naturally-occurring clays which can be composited with the zeolite include those of the montmorillonite and kaolin families, which families include the sub-bentonites and the kaolins commonly known as Dixie, McNamee-Georgia and Florida clays or others in which the main mineral constituent is haloysite, kaolinite, dickite, nacrite or anauxite. Such clays can be used in the raw state as originally mined or initially subjected to calcination, acid treatment or chemical modification.

In addition to the foregoing materials, the zeolite employed herein can be composited with a porous matrix material such as carbon, alumina, titania, zirconia, silica, silica-alumina, silica-magnesia, silica-zirconia, silica-thoria, silica-beryllia, silica-titania, etc., as well as ternary oxide composition, such as silica-alumina-thoria, silica-alumina-zirconia, silica-alumina-magnesia, silica-magnesia-zirconia, etc.. The matrix can be in the form of a cogel. The relative proportions of zeolite component and matrix material, on an anhydrous basis, can vary widely with the zeolite content ranging from between 1 to about 99 wt. %, and more usually in the range of about 5 to about 90 wt. % of the dry composite.

A series of experiments have been carried out to illustrate the process of the instant invention and compare the results of that process with the results of the prior art process for propylene hydration using ZSM-5 catalyst. The operating conditions and results of the present process are depicted in Table 1 as Examples 1–3 for propylene hydration catalyzed by acidic ZSM-5 and Examples 4–5 for propylene hydration catalyzed by acidic ZSM-35. The operating conditions and results of the prior art process are depicted in Table 1 as Experiments 1 and 2 for propylene hydration catalyzed by acidic ZSM-5.

TABLE 1

Propylene Hydration Over ZSM-5 & ZSM-35; Productivity Comparison

| | Invention Examples | | | | | Prior Art Experiments | |
|---|---|---|---|---|---|---|---|
| | 1 | 2 | 3 | 4 | 5 | 1 | 2 |
| Hrs on stream | 38 | 158 | 264 | — | — | 20 | 44 |
| Catalyst | ZSM-5 | ZSM-5 | ZSM-5 | ZSM-35 | ZSM-35 | ZSM-5 | ZSM-5 |
| $H_2O/C_3^=$ | 0.18 | 0.18 | 0.33 | 0.2 | 0.4 | 2.0 | 0.5 |
| P(kPa) | 2800 | 4900 | 4900 | 4900 | 4900 | 7000 | 7000 |
| T(°C.) | 150 | 193 | 193 | 193 | 193 | 165 | 165 |
| WHSV | 8.42 | 8.42 | 7.83 | 8 | 8 | 0.78 | 0.51 |
| Productivity(a) | 0.12 | 0.66 | 0.66 | 2 | 1.3 | 0.034 | 0.012 |
| Selectivity(b) | 100% | 73.4% | 97.6% | >99% | >99% | 100% | 100% |
| wt % IPA | 1.4 | 5.8 | 8.3 | 7.0 | 15.0 | | |
| wt % DIPE | 0.0 | 2.1 | 0.2 | 0.0 | 0.0 | | |

(a) grams of oxygenates/g cat × hr
(b) 100 × (grams of IPA)/(grams of IPA + DIPE)

Referring now to the Figure, an illustration is presented showing the stability of ZSM-5 at 4,900 kPa, 193° C. and a water/propylene mole ratio (Q) of 0.18. Within experimental error, oxygenate productivity remained constant over the course of six days (70 to 170 hours-on stream). To maintain the demonstrated stability, it is necessary to use medium pore zeolites and to prevent the presence of a liquid aqueous phase which dealuminates the catalyst.

What is claimed is:

1. A process for the production of isopropanol with high selectivity, high catalyst productivity and long catalyst life comprising:

contacting water and a feedstream comprising propylene in the gas phase with acidic medium pore, shape selective metallo-silicate catalyst particles under propylene hydration conditions at a water:propylene mole ratio between 0.05 and 0.499, whereby said isopropanol is produced at a selectivity of at least 70 weight percent and catalyst productivity is at least 0.1 unit weight of oxygenates comprising isopropanol/unit weight of catalyst per hour.

2. The process of claim 1 wherein said metallosilicate catalyst particles comprise aluminosilicate zeolites.

3. The process of claim 1 wherein said mole ratio is between 0.1 and 0.35.

4. The process of claim 1 wherein said catalyst comprises ZSM-5 and said mole ratio is between 0.18 and 0.33.

5. The process of claim 1 wherein said conditions comprise temperature between 50° C. and 450° C., pressure between 700 kPa and 24,000 kPa weight hourly space velocity between 0.1 and 50.

6. The process of claim 5 wherein said temperature is between 150° C. and 250° C., pressure is between 2800 kPa and 7000 kPa and weight hourly space velocity is between 1 and 10.

7. The process of claim 6 wherein said catalyst productivity is at least 0.5 unit weight of said oxygenates per unit weight of catalyst per hour at a catalyst life of greater than 20 hours-on-stream.

8. The process of claim 7 wherein said catalyst life is at least 400 hours.

9. A process for the production of isopropanol comprising:

contacting a gaseous feedstream comprising water and propylene with acidic medium pore, shape selective metallo-silicate catalyst particles selected from the group consisting of ZSM-5, ZSM-11, ZSM-12, ZSM-22, ZSM-23, ZSM-35 and Ferrierite under propylene hydration conditions comprising a water:propylene mole ratio between 0.1 and 0.35, temperature between 50° C. and 450° C., pressure sufficient to avoid exceeding the dew point of water and weight hourly space velocity between 1 and 10, whereby said isopropanol is produced at a selectivity of at least 70 weight percent, catalyst productivity is at least 0.1 unit weight of oxygenates comprising said isopropanol per unit weight of catalyst per hour and catalyst life is at least 170 hours-on-stream.

10. The process of claim 9 wherein said mole ratio is between 0.18 and 0.33 and said temperature is between 150° C. and 205° C.

* * * * *